United States Patent [19]
Fryklund et al.

[11] Patent Number: 5,068,224
[45] Date of Patent: Nov. 26, 1991

[54] METHOD OF IMPROVING REGENERATION OF TRANSFECTED PERIPHERAL NERVES USING IGF-1

[75] Inventors: Linda Fryklund, Sollentuna; Hans A. Hansson, Hovas; Martin Kanje, Sodra Sandby; Anna Skottner, Ekero, all of Sweden

[73] Assignee: KabiVitrum AB, Sweden

[21] Appl. No.: 245,146

[22] Filed: Sep. 16, 1988

[30] Foreign Application Priority Data

Sep. 18, 1987 [SE] Sweden ................................. 8703625

[51] Int. Cl.$^5$ ............................................. A61K 37/24
[52] U.S. Cl. ........................................ 514/21; 514/3; 514/4; 514/12
[58] Field of Search ........................... 514/3, 4, 12, 21

[56] References Cited

FOREIGN PATENT DOCUMENTS 0128733 12/1984 European Pat. Off. .

OTHER PUBLICATIONS

Acta Physiol. Scand., 126, 1986, H. A. Hansson et al., "Evidence Indicating Trophic Importance of IG F-1 in Regenerating Peripheral Nerves", pp. 609–614.
Cell and Tissue Research, 247/1987), H.-A. Hansson et al., "Rapid Exoplasmic Transport of Insulin-Like Growth Factor I in the Sciatic Nerve of Adult Rats", pp. 241–247.
Nature, vol. 296, Mar. 18, 1982, E. Schoenle et al., "Insulin-Like Growth Factor I Stimulates Growth in Hypophysectomized Rats", pp. 252–253.
The Journal of Neuroscience, 6(5), May 1986, E. Recio-Pinto et al., "Effects of Insulin-Like Growth Factor-II, and Nerve Growth Factor on Neurite Formation and Survival in Cultured Sympathetic and Sensory Neurons", pp. 1211–1219.
Intern. J. Neuroscience, vol. 26, 1985, D. N. Ishii et al., "Neurite Formation Modulated by Nerve Growth Factor, Insulin, and Tumor Promoter Receptors", pp. 109–127.
Proc. Natl. Acad. Sci., USA, vol. 73, No. 7, Jul. 1976, E. Rinderknecht et al., "Polypeptides with Nonsuppressible Insulin-Like and Cell-Growth Promoting Activities in Human Serum: Isolation, Chemical Characterization, and Some Biological Properties of Forms I and II", pp. 2365–2369.
Proc. Natl. Acad. Sci., USA, vol. 73, No. 12, Dec. 1976, E. Rinderknecht et al., "Amino-Terminal Sequences of Two Polypeptides from Human Serum with Nonsuppressible Insulin-Like and Cell-Growth-Promoting Activities: Evidence for Structural Homology with Insulin B Chain", pp. 4379–4381.
Jour. of Neuro-Science Research 8(1982), M. Bothwell, "Insulin and Somatemedin MSA Promote Nerve Growth Factor-Independent Neurite Formation by Cultured Chick Dorsal Root Ganglionic Sensory Neurons", pp. 225–231.
Jennische et al., Acta Physiol. Scand., Jan. 1987, 129, pp. 9–15.
Hansson et al., Acta Physiol. Scand., Feb. 1987, pp. 165–169.

*Primary Examiner*—F. T. Moezie
*Attorney, Agent, or Firm*—Pollock, Vande Sande & Priddy

[57] ABSTRACT

A method for improving the regeneration of transected peripheral nerves in mammals and man, by administering a sufficient amount of insulin-like growth factor 1 (IGF-1) to a mammalian host in need of such treatment. If desired, administration of the medicament containing insulin like growth factor can be carried out locally by infusion.

6 Claims, No Drawings

METHOD OF IMPROVING REGENERATION OF TRANSFECTED PERIPHERAL NERVES USING IGF-1

FIELD OF THE INVENTION

The present invention relates to improvements in the regeneration of transected peripheral nerves in mammals.

BACKGROUND OF THE INVENTION

Structure and function of the peripheral and autonomic nervous systems

The peripheral and autonomic nervous systems are formed by nerve cell bodies and processes, i.e. axons and dendrites forming bundles, innervating the skin, skeletal muscles, glands and related structures. The nerve cell bodies are situated in the brain, spinal cord or in ganglia. Each myelinated nerve fiber is enveloped by Schwann cells while in cases of unmyelinated fibers several axons are enclosed in each Schwann cell. The Schwann cells are enveloped by basement membrane, some extracellular matrix and an endoneurial mesenchymal sheath. Many such units form a nerve, which is limited by perineurium of collagen, fibroblasts and related cells. An epineurium encloses the whole nerve, mostly comprising several nerve fascicles. A blood-nerve barrier prevents plasma proteins and many other substances from unrestricted penetration among the nerve fascicles. Motor and sensory nerves have the same structure but differ with regard to the axon and myelin dimensions. This means that in a mixed peripheral nerve it is not possible by the morphological characteristics to state whether a single axon is afferent or efferent.

Autonomic nerve fibers, sympathetic and parasympathetic, are accompanying the sensory and motor nerve fibers as well as blood vessels.

Aspects on development of the nervous system

Nerve cells and their supporting neuroglial cells are derived from the neuroectoderm. Although originally having a common embryonic origin, the nerve cells at an early stage differentiate and obtain their structural characteristics. Hamburger and Levi-Montalcini almost 40 years ago demonstrated that the development of neurons are dependent on their target structures in order not to degenerate after differentiation. They provided direct evidence that neurons may die during normal development if not gaining synaptic contacts. This is true both for the central, peripheral and autonomic nervous systems. These observations eventually formed the background to the demonstration by Levi-Montalcini and coworkers (J Exp Zool 116, 321-362, 1951) of important trophic factors, released from the target organs to the neurons, necessary for survival.

The nerve cells in the central and peripheral nervous system reach their final number at about birth in mammals. The regenerative capacity present for peripheral and autonomic nerves during childhood is reduced with increasing age. This means that no new nerve cells are formed after birth, although axons and dendrites may regenerate to a limited extent. The autonomic system has a much higher regenerative capacity than the peripheral nervous system.

Normal regeneration of peripheral nerves

Injury to peripheral and autonomic nerves results in degeneration of the distal parts of the axons and dendrites. The Wallerian degeneration, following, results in hypertrophy and hyperplasia of the Schwann cells lining the distal nerve. The proximal end of the injured axons retract to variable extent, and, after a short lag period, the repair processes start. Sprouts with finger-like extensions form a leading part of the outgrowing cell processes, the path of which is guided by the reactive Schwann cells. In most systems the rate of regeneration is in the range of 1-2 mm/day. Higher values have been documented for the autonomic nervous system. However, after about a month, depending on the test system examined, the rate of regeneration seems to be slowed down and, eventually, cease. Little is known about the mechanisms regulating the rate of regeneration. Redistribution of axoplasmic material, including the axolemma, seems to prevail. Detailed knowledge of several important aspects on mechanisms for the regenerative process is unknown.

Model systems in vivo for experimental studies of nerve regeneration

Extensive studies have been performed on the regeneration of mainly peripheral nerves after various types of experimental injuries.

Nerve crush is an injury of moderate severity, mostly resulting in complete recovery of the structure and function of injured axons and dendrites. It has been established that continuity of the basement membrane as well as early reestablishment of the microcirculation in peripheral nerves after crush injury is a prerequisite for complete recovery. Discontinuities in the basement membrane or even limited persistent blood vessel damage delay or impair the recovery.

Sectioning of a nerve results in discontinuity of the epi-, peri- and endoneuriums, as well as of the basement membrane enveloping the supporting Schwann cells with the enclosed axons and dendrites. Extensive vascular damage occurs as well. In the latter cases nerve regeneration starts after a delay of a few days in most clinical and experimental systems using peripheral nerves. Even meticulous microsurgery, almost reestablishing continuity nerve fascicle by nerve fascicle, is not sufficient to gain any major improvement of the regeneration. Removal of the peri- and/or epineurum neither improves the extent of nerve regeneration, structurally or functionally. Most techniques used results in limited improvement as compared to if the nerve ends remained apposed. Further complications occurring in cases of sectioned peripheral nerves are e.g. the formation of neuroma and fibrous scar tissue starting after about a week. This eventually results in formation of neuroma and permanent deficient function of the nerves. Concomitantly, nerve cell regeneration takes place, to a variable extent, in the brain, spinal cord and spinal ganglia may further result in permanently deficient nerve function.

Demyelination

Demyelination of the peripheral nerves induced by ischemia, sometimes combined with pressure injuries or caused by chemical agents like isoniazide and related drugs, results in segmental nerve damage. This impairs the nerve function and may result in progressive structural degenerative changes of nerve fibers. However, if the continuity of the basement membrane encircling the fascicles is retained, and there is adequate microcirculation, axons and dendrites regenerate per cuntinuum in their original trail. Functional and structural recovery is often gained. Other chemical agents, like hexachlorophene and heavy metal compounds, induce segmental degeneration of myelin and supporting glial cells, sometimes advancing from the periphery towards the more central part of the peripheral nervous system. Even in these cases regeneration is attainable if the continuity of the fascicles and if the circulation is retained. The peripheral and autonomic nerves are to a major extent able to regenerate to full extent, if continuity of fascicles and appropriate microcirculation after dismission of the causing agent.

Immunological methods have been used to induce degeneration of Schwann cells and/or myelin, followed by regeneration. Infections with certain virus or exposure to microbial toxins may similarly cause more or less extensive nerve damage. However, in these cases appropriate recovery of the structure and function of axons and dendrites are mostly obtained if the nerve fascicles are in continuity and the impairment of the microcirculation in the nerves is limited in severity.

It may be concluded that physical, microbiological, immunological and toxic agents may cause degeneration of nerve fascicles, and that regeneration may be possible if the continuity of the fascicles is not broken, and the microcirculation adequate. An important factor seems to be that the basement membrane, enveloping the Schwann cells, are remaining intact. Prolonged exposure to noxious agents may eventually result in disintegration of the basement membrane, resulting in impaired and delayed structural and functional recovery of nerves. The same is true for the microcirculation, which obviously plays a key role for the ultimate result.

Effects of damage to innervated structures

Adequate function of the target innervated by peripheral and autonomic nerves seems to be a prerequisite for maintenance of the function of the peripheral and autonomic neurons. Hamburger & coworkers made important contributions in establishing that neurons depend on their targets for their survival. This means that damage to skeletal muscle cells, integumentum or glands results in disconnection of synapses from the target organ and more or less extensive degeneration of at least the distal parts of axons and dendrites. The degeneration may be of such extent that even neurons are lost. Recovery of the target organ may result in recovery of function after appropriate regeneration. Even in such cases, continuity of the fascicles, at least to the close vicinity of the target organs, and adequate microcirculation seems to be a prerequisite for successful regeneration.

Techniques to improve regeneration of peripheral autonomic nerves

Most published works are dealing with peripheral nerves, reflecting their importance for normal motor and sensory functions. The autonomic nerve fibers have, however, under normal circumstances, higher ability to regenerate than peripheral nerves. However, it is likely that similar conditions prevail for both peripheral and autonomic nerves.

Microsurgery

During the last decade the use of microscope and microsurgical techniques when doing nerve sutures has increased extensively. Methods have been devised for meticulous repair of injured peripheral nerves. However, the improvement gained has been limited, in spite of careful microsurgical reestablishment of connections between the nerve ends. Obviously, reestablishment of close contact is not enough for successful nerve regeneration.

Guides for nerve regeneration

Several techniques have been established since the pioneering work almost a century ago by J Forssman, who demonstrated improved regeneration of peripheral nerves by using a reed as a guide. After that, several similar devices have been assigned, aimed to improve the nerve regeneration. Lundborg & Hansson (Brain Res 178, 573–576, 1979) developed a technique using a pseudomesothelial-lined chamber which obviously improved to some extent the nerve regeneration. Silicon tubes and tubes of biodegradable material have further been developed and extensively used.

All these techniques seem to have in common that they improve the initial outcome of the nerve regeneration, mostly due to reduction in the extent of neuroma formation. In several reports significant although minor improvements could be demonstrated with regard to the number of nerve fibers reestablishing contact as well as increase in myelination and diameter of the axons. Unfortunately, a considerable proportion of the nerve fibers fail or cease to regenerate, and do not establish synaptic contacts. There does not seem to be any difference between motor nerve fibers and sensory ones. This means that although structural contacts may be reestablished, deficiency in function persists. Furthermore, the long time taken for the nerve regeneration results in atrophy and even extensive degeneration of target tissues such as skeletal muscles and skin structures, including glands and receptors. Conditioning lesions have further been used to improve regeneration of peripheral nerves. Thus, the longer the distance and the more extensive the damage, the less impressive have been the benefits obtained using either technique for improving nerve regeneration. Obviously, some supporting, additional stimuli are lacking.

Extracellular matrix components, such as fibronectin and laminin, are substances isolated from basement membranes and associated structures in peripheral nerves. Reconstitution of such purified proteins and glycoproteins have been done and demonstrated in vitro to enhance nerve regeneration. However, the results obtained so far from studies in vivo have not reached the promising levels indicated by tissue culture studies. Extensive work is still demanded before it is possible to establish whether in animals and humans, fibronectin and laminin and related substances per se improve the acute and long-term results with regard to regeneration of peripheral nerves.

Growth factors

Levi-Montalcini & Hamburger (1951) established that a nerve growth factor may be formed under certain circumstances, improving regeneration of fetal sensory and autonomic neurons. After extensive studies nerve growth factor (NGF) was identified and characterized. NGF has been demonstrated to be of importance for especially sympathetic neurons, but also for sensory nerve cells during their development. However, available data seem to indicate that in young and adult mammals NGF is not required by motor and sensory neurons for their survival, with the exception of some sympathetic autonomic neurons. It has been established by hybridization techniques that target organs may synthetize NGF, which is then taken up and transported in retrograde direction to the soma of certain neurons. However, motor neurons fail to take up NGF, which thus is no trophic factor for the peripheral nervous system. Infusion of NGF has been tested by several groups using different model systems. So far, no significant improvement has been established for peripheral sensory or motor neurons in vivo for young and adult mammals. Some improvements have been reported for autonomic neurons and for certain clusters of neurons in the brain. Other factors such as vitamin B, CAMP, gangliosides, testosterone, ACTH and thyroid hormones, have been tested with regard to their ability to improve nerve regeneration in vitro and in vivo. Several substances have been reported to be beneficial in tissue culture systems. However, no consistent improvement of the acute or long-term outcome of regeneration of peripheral nerves has so far been demonstrated by several independent research teams in vivo for young and/or adult mammals.

It has, however, recently been shown that also both insulin and insulin-like growth factors may have influence on neurite formation in vitro (Bothwell, J. Neurosci. Res. 8, 225–231, 1982; Ishii et al, Intern. J. Neurosci. 26, 109–127, 1985; Recio-Pinto et al, J. Neurosci. 6 (5), 1211–1219, 1986). It has also been shown by Sara et al (Acta Physiol. Scand. 115, 467–470, 1982) that somatomedins (insulin-like growth factors I and II), measured by radioreceptor assay, were found both in the CNS and peripherally in sciatic nerves of cats.

Schwann cells in reactive nerves, injured by sectioning or by crush, exert positive influence on the regeneration of peripheral nerve fibers. Crush of a nerve 2 weeks prior to a second injury results in improved regeneration as compared to "non-primed" nerves. Similarly, the use of a distal sciatic nerve as a target in chamber systems improves the regeneration of the sciatic nerve in rats. Predegeneration of the target nerve by injury one or 2 weeks prior to reestablishment of contact thus induces formation of factors seemingly improving long-term degeneration. Several different experimental systems have been established by various groups during the last decades. However, no specific factors have yet been identified or demonstrated to be responsible for the improved nerve regeneration.

By immunohistochemical techniques Hansson et al have shown (Acta Physiol. Scand. 126, 609–614, 1986) that insulin-like growth factor I (IGF-1) is mainly found in the Schwann cells after injury but also extra cellularly in the growth cone of the regenerating nerve. IGF-1 was also observed in the nerve cell bodies of the anterior horns of the lumbar spinal cord and in spinal and autonomic ganglia. Hansson et al also showed (Cell Tissue Res. 247, 241–247, 1987) that IGF-1 was transported at rapid axoplasmic rate mainly in the anterograde direction, but also, although to a lesser extent, retrogradely. IGF-1 has also been shown to stimulate the development of oligodendrocytes, indicating a possible effect of IGF-1 on myelination.

SUMMARY OF THE BACKGROUND OF THE INVENTION

It has been estimated that only in Sweden several thousand cases of mainly nerve damage in the extremities and face are of such clinical importance that they call for surgical interventions to improve the final outcome. The methods used, however, ranging from meticulous surgery to conservative treatment, have not improved to any major extent the long-term results of nerve function. Against this clinical background it is very important to improve the conditions for regeneration of peripheral as well as autonomic nerves to gain better final results after injury to major nerves, for the benefit of the quality of life for patients. The present invention will provide such improvement in the regeneration of peripheral nerves in mammals and man.

THE INVENTION

It has been found according to the present invention that insulin-like growth factor 1 (IGF-1) can be used to increase regeneration of transected peripheral nerves and to decrease the persistance of permanent nerve function deficiency. Specific areas where it is important to establish nerve regeneration is for example hand- and face surgery (in many cases due to accidents), where no clinical improvements regarding long-term effects on nerve function have been done up to date.

It is also important to improve nerve regeneration after surgical removal of tumors close to or involving peripheral nerves innervating specific target organs. Furthermore, reestablishment of innervation of transplanted skin is another important area.

In all cases it is of utmost importance to increase the rate of peripheral nerve regeneration, making the nerve reach its target organ as quickly as possible, to be able to improve the possibility of full recovery after an injury, involving transection of peripheral nerves.

In one aspect, the invention provides a method for improving the regeneration of transected peripheral nerves in mammals and man, by administering a sufficient amount of insulin-like growth factor 1 (IGF-1) to a mammalian or human host in need of such treatment. The administration can be made e.g. by local administration to the affected area or by adminstration of IGF-1 to ganglia in the affected nerves.

In another aspect the invention relates to the use of insulin-like growth factor 1 (IGF-1) in the manufacture of a medicament for increasing the regeneration of transected peripheral nerves.

The insulin-like growth factor 1 (IGF-1) is a substance which is known in the art.

In clinical practice, IGF-1 can be administered by infusion, or by local- applications to the affected area. A further mode of administration of IGF-1 is via the ganglia of the affected nerves, whereby the remaining part of the nerve will transport IGF-1 to the nerve end.

The amount in which IGF-1 is administered will vary within a wide range and will depend on the circumstances such as the kind and localization of the damaged nerves. The treatment may have to be continued for several days and weeks until the desired therapeutical result has been obtained. The aim is to obtain a full regeneration of the lost part of the nerve.

EXPERIMENTS USING IGF-1 TO PROMOTE REGENERATION IN PERIPHERAL NERVES IN VIVO

We have performed three main types of experiments on the growthpromoting effects of IGF-1 in injured, regenerating sciatic nerve in rats.

A. Long-term effects of IGF-1 infusion

A1. Test method

A chamber made of silicone was surgically implanted in the thigh of the hind legs of adult male rats (body weight 250 g). Within the silicone chamber a Y-shaped tunnel was drilled with a diameter of 1.8 mm. Thus three interconnected trails and openings were present in the silicone chamber. These silicone chambers allow regeneration of the nerve from one trail into either of the other two. Thus, it is possible to test for preference of growing nerve fibers for various targets.

The left sciatic nerve was cut on anaesthetized rats and the proximal end inserted one mm into one of the tunnels and sutured. A miniosmotic pump (Alza, model 2001) was connected to a second opening, while the third was left open. The miniosmotic pump was designed to deliver fluid at a rate of about 1 $\mu$l/hour for 2 weeks. The insulin-like growth factor 1 (IGF-1) used in the experiments has been produced in known manner according to DNA technology and was purified by conventional biochemical techniques.

The following solutions were used to test for possible trophic influence of added substances on the regeneration of the sciatic nerve fibers into the silicone implant:
1. Saline buffered with 10 mM phosphate buffer.
2. 1% bovine serum albumin (BSA) in buffered saline.
3. IGF-1 at a concentration of 250 $\mu$g/ml in sterile purified water (batch 2043:2, KabiVitrum AB, Stockholm, Sweden).
4. IGF-1 dissolved in sterile non-pyrogenic water at a concentration of 100 $\mu$g/ml.
5. The distal sciatic nerve was sutured to one opening and a miniosmotic pump to another, delivering 100$\mu$g/ml IGF-1.
6. A segment of the anterior tibialis tendon was sutured to one opening and a miniosmotic pump to another, delivering 1 $\mu$l/h of 100 $\mu$g/ml of IGF-1.

Great care was taken to avoid infection or bleedings during the surgery. The rats were allowed to move freely for either 2 or 4 weeks after the surgery.

At the time of analysis the animals were anaesthetized and the chamber with surrounding tissue exposed, dissected and fixed by immersion in buffered glutaraldehyde. The transparent chambers were carefully inspected and the different nerve segments were carefully evaluated, photographed, postfixed in buffered osmium tetroxide and then embedded in Epon for sectioning for light- and electron microscopic analysis. The ingrowth of tissue was measured both by macroscopic inspection and by light microscopy of sections prepared from every millimeter segment of the tissue in the chamber. Selected specimens were further prepared for electron microscopy and contrasted by uranyl acetate and lead citrate prior to evaluation in a JEOL 100 CX TEM-SCAN.

Morphometric evaluation of the dimensions of axons, myelin and surrounding structures are in progress using an IBAS I & II system (Zeiss-Kontron).

RESULTS

The results of our present study may be summarized as follows. Infusion of IGF-1 for 2 weeks (N:4) or 4 weeks (N:7), at a concentration of 100 $\mu$g/ml and 1 $\mu$l/h enhances the outgrowth of the nerve fibers from the proximal end of the sciatic nerves. The front of the ingrowing nerve fibers reached in 2 weeks a distance of 7-8 mm, and after 4 weeks 8-16 mm. Both unmyelinated and myelinated nerve fibers were recognized. There were no necrotic areas, neither any signs of degeneration. Loose connective tissue surrounded the outgrowing nerve fibers. Similar results were obtained using IGF-1 at a concentration of 250 $\mu$g/ml for 4 w. Higher concentrations, i.e. 1000 $\mu$g/ml were used in pilot experiments, but found to cause invasion of numerous macrophages, and did not promote nerve regeneration. The controls, i.e. addition of saline or BSA to the silicone chamber induced in the present study regeneration only for about 1 mm at maximum. Addition of a peripheral segment of the sciatic nerve or a piece of tendon to one opening of the Y-shaped chamber and concomitant infusion of IGF-1 resulted in as extensive ingrowth as IGF-I infusion per se.

Electron microscopic examination of the regenerating sciatic nerves revealed that the newly formed axons after 4 weeks to a large extent were enveloped by myelin of normal structure and dimensions. There was no sign of ultrastructural abnormalities in the axoplasm, i.e. microtubules and filaments formed the dominating elements but endoplasmic reticulum, vesicles and mitochondria were observed in normal extent. The Schwann cells in the IGF-1 treated nerves showed, however, signs of hyperplasia and hypertrophy. Their cytoplasm was extensive as compared to the controls. The endoplasmic reticulum, ribosomes, mitochondria and Golgi complexes were strikingly extensive. Basement membrane was formed at the front of the outgrowing nerve as were minifascicles, delimited by endo- and perineurial tissue. Extensive neovascularization was evident. In contrast, silicone chambers only infused with saline or BSA lacked signs of regeneration of nerve fibers. Their Schwann cells appeared inactive, sometimes containing vescicles in increased frequency. Macrophages were common. There was no neovascularization.

It may be concluded that the results obtained distinctly demonstrate that IGF-1 promotes regeneration of transected sciatic nerve in a silicon chamber. Very high concentrations seem to induce invasion of macrophages—these latter results need further evaluation. Optimal concentrations of IGF-1 seem to be in the range of 100-250 $\mu$g/ml, infused at 1 $\mu$l/h.

A2 Test method

Sciatic nerves were cut and inserted into a 20 mm long silicone tube, to which a miniosmotic pump was connected. The small hole on the wall at about the middle of the tube served as an outlet for excess fluid from the chamber system and the pump. Pilot experiments were performed using 250 $\mu$g/ml or 100 $\mu$g/ml, delivered by a pump with a pump rate of 1 $\mu$l/h and the volume of 230 $\mu$l, i.e. pumping for about 2 w. The silicone tube and its attached miniosmotic pump were placed subcutaneously on the left hind leg of anaesthetized rats.

Test results

These pilot experiments demonstrated similarly improved nerve regeneration was obtained when infusing IGF-1 (100 μg/ml and 250 μg/ml; infusion rate 1 μl/h) as compared to that when using buffered saline.

B. Specificity of IGF-1 effects on peripheral nerve regeneration

B1 Test method

Animals

Female Sprague-Dawley (Alab, Sweden) rats weighing approximately 200 g were used for the experiments. The rats were kept in transparent cages on a 12h-12h light and dark cycle. Commercial laboratory food and water was freely available.

Rats were anaesthetized with an intraperitoneal injection of 0.3 ml of a mixture of pentoparbital (60 mg/ml), diazepam 5 mg/ml and saline in 1:2:1 volume proportions.

Silicone tube chambers

Silicone tube chambers (STC) were made of medical grade silicone tubing (Mentor Co.) with an outer diameter of 3.0 mm and an inner diameter of 1.8 mm as depicted in FIG. 1. The corresponding measures of the outlet were 2.0 mm and 1.2 mm respectively. The distal end of the STC was attached to a miniosmotic pump Alzet type 2001 via a silicone catheter. The catheter was glued to the STC with silicone glue (Tremco).

Antibodies

Antibodies to IGF-1 were raised in rabbits against a semipure preparation of plasma-derived human IGF-1. The antiserum (k624) was of a relatively low titer and had a cross reactivity with IGF-II of $\leq 5\%$, and with insulin $<1\%$. Antibodies to porcine insulin raised in rabbits were purchased from Novo.

Operations

The sciatic nerve was exposed in the thigh and transected at the level of the knee. The nerve was crushed 10-18 mm proximal to the transsection with specially designed pliers. The crush site was labelled by attaching a 9-0 suture to the epineurium. A small piece of muscle was cut from the thigh and sutured to the proximal end of the STC in order to prevent leakage. Another 9-0 suture was attached to the epineurium at the site of the transsection. The nerve was then forced into the STC and secured in place by suturing the terminal end of nerve to the STC wall. The STC was filled with serum from IGF-1 immunized or unimmunized rabbits diluted 1:25 in a modified Ringer solution (139 mM NaCl, 2.4 mM KCl, 1.4 mM CaCl$_2$, 2 mM MgSO$_4$, 0.6 mM NaH$_2$PO$_4$, 3,25 mM Na$_2$HPO$_4$ pH 7.4) or in saline. The distal end of the STC was attached via a catheter to the miniosmotic pump. The miniosmotic pump and its catheter were placed subcutaneously in the abdominal region of the rat. The catheter was introduced subcutaneously and connected to the STC. The wounds were then closed by sutures. The outlet from the STC penetrated the skin and was open to the air on the outside of the animal. The rats were then left for up to 6 days.

Evaluation of regeneration

Regeneration was evaluated with the "pinch-test" as described (Lubinska L & Olekiewicz M, Acta Biolog Exp 15(10), 125-145, 1950). The rats were anaesthetized, the sciatic nerve exposed in the thigh region, and the STC removed. Consecutive segments of the sciatic nerve were pinched with a pair of forceps, starting from the distal end. When the regenerated sensory axons were crushed they elicited a reflex response noted as a contraction of the muscles on the back. The distance between this site and that of the original crush, previously labelled with a suture, was taken as the regeneration distance.

Test results

Regeneration

The normal rate of regeneration in the control rats, treated only with saline, was 1.7 mm/day during a 6 days' period. Histopathological evaluation showed active regenerating cells in the nerve tissue, and some inflammatory cells.

In rats treated with IGF-1 (100 μg/ml) a significant increase in the length of regeneration was observed already at days 1 and 2, which indicated that addition of the peptide to the nerve tissue induced a more rapid start of regeneration. Histopathological evaluation did show a moderate degree of inflammation in the nerve segments after long exposure to IGF-1 ($>5$ days; table 1). NGF did not stimulate the regeneration when added to the perfusion chamber (table I).

Table II shows the effects of rabbit serum with and without IGF-1 antibodies on regeneration in the STC. Perfusion with normal serum at a dilution of 1:25 did not affect regeneration during a 4 days' period. In contrast, regeneration was inhibited by perfusion with serum containing IGF-1 antibodies. This inhibition could be overcome by adding IGF-1 to the miniosmotic pump.

Perfusion of the nerve segments with serum containing antibodies to insulin failed to affect regeneration of the rat sciatic nerve.

Discussion of the test results

When the silicone chambers were perfused with saline, regeneration was normal throughout the experimental period.

Regeneration with IGF-1 present in the chambers was significantly increased compared to control rats at all time points.

Perfusion of the regenerating rat sciatic nerve with IGF-1 antibodies was found to inhibit regeneration. This inhibition appeared specific since it could be overcome by addition of IGF-1 and since antibodies raised towards insulin did not affect regeneration. This suggests that endogenous IGF-1 is required for normal regeneration. Antibodies are high molecular weight proteins which do not readily penetrate into cells, suggesting that neutralization of extracellular IGF-1, by the antiserum, is responsible for the observed inhibition. The site and mechanism of IGF-1 action are unknown. It has been found to stimulate proliferation of various cell types. Schwann cell proliferation is induced in the distal segments of a regenerating peripheral nerve. If this proliferation is blocked, regeneration is impeded.

C. Ganglionic application of IGF-1

Test method

Both sciatic nerves were crushed. A miniosmotic pump Alzet 2001 filled with IGF-1 (50 μg/ml) was placed subcutaneously on the back of the animals. A catheter was attached to the pump. The catheter-outlet was fixed by sutures unilaterally close to the dorsal root ganglia of the sciatic nerve. Regeneration distances on the IGF-1 treated side (IGF-1) and the contralateral nerve (contralateral) were evaluated 4 days later.

Test results

The test results are given in table III. The ganglionic application of IGF-1 significantly increased regeneration distances compared to untreated nerve.

The regenerating neurites are more permeable to drugs and appear to be able to pick up molecules from its surrounding. It is possible that extracellular IGF-1 in the distal nerve segment can be internalized in the regenerating neurites and reach the neuronal cell body via retrograde axonal transport. Retrograde axonal transport of IGF-1 has been demonstrated, but whether or not IGF-1 has been produced in the neuron or has been taken up by the neurites is not known. However, the finding that ganglionic application of IGF-1 also increases regeneration suggests that the neuronal cell body could be a main target for IGF-1 action.

Conclusions

Peripheral nerves from young and adult mammals regenerate incompletely, especially if the nerve had to bridge longer distances. The slow rate of regeneration is further reduced with time.

The target structures, e.g. skeletal muscles, glands, skin receptors, may degenerate extensively if left for longer time periods without innervation, calling for better techniques for improvement of longterm functional results.

Regeneration of peripheral nerves in humans form an important clinical problem urging for improvement in treatment.

Thus, IGF-1 has been demonstrated to be beneficial for improving the regeneration of transected peripheral nerves.

TABLE I

EFFECTS OF NGF ON REGENERATION DISTANCES IN THE RAT SCIATIC NERVE

| Treatment | | 4 days |
|---|---|---|
| NGF 2.5 S | 25 ng/ml | $7.5 \pm 0.5$ |
| | 250 ng/ml | $6.6 \pm 1.3$ |
| | 2500 ng/ml | $7.0 \pm 1.2$ |

Regeneration distances in (mm), Mean value ± SD (N)

TABLE II

EFFECTS OF ANTI-IGF-1 SERUM ON REGENERATION DISTANCES IN THE RAT SCIATIC NERVE

| Treatment | Dilution | 3 days | 4 days |
|---|---|---|---|
| Control serum | 1:25 | $3.8 \pm 0.4$ (6) | $8.0 \pm 0.6$ (5) |
| Control serum + IGF-1 5 μg/ml | | $4.0 \pm 0.2$ (4) | $7.0 \pm 1.6$ (6) |
| anti-IGF-1 serum | 1:25 | $2.3 \pm 1.0^*$ (5) | $4.8 \pm 2.2^*$ (4) |
| anti-IGF-1 serum + IGF-1 5 μg/ml | | — | $7.9 \pm 0.4$ (3) |
| anti-IGF-1 serum + IGF-1 25 μg/ml | | — | $8.2 \pm 0.3$ (3) |
| anti-insulin serum | 1:25 | — | $8.3 \pm 0.3$ (2) |

Regeneration distances in (mm), mean values ± SD. (N).
*$P < 0.05$

TABLE III

EFFECTS OF GANGLIONIC APPLICATION OF IGF-1 ON REGENERATION OF THE RAT SCIATIC NERVE

| | | Regeneration distances (mm) | Ratio IGF-1/contralateral |
|---|---|---|---|
| Rat 1 | contralateral | 7.6 | 1.17 |
| | IGF-1 | 8.9 | |
| Rat 2 | contralateral | 7.8 | 1.10 |
| | IGF-1 | 8.6 | |
| Rat 3 | contralateral | 7.9 | 1.24 |
| | IGF-1 | 9.8 | |
| | | | Mean: $1.17 \pm 0.07^*$ |

*one tailed t-test $P < 0.05$

What we claim is:

1. A method for improving the regeneration of transected peripheral nerves in mammals, by administering a therapeutically effective amount of insulin-like growth factor I (IGF-1) to ganglia in the affected nerves of a mammalian host in need of such treatment.

2. The method of claim 1, wherein said mammalian host is a human.

3. A method for improving the regeneration of transected peripheral nerves in mammals, by administering locally a medicament containing 100–250 μg/ml of insulin-like growth factor I (IGF-I) to provide a sufficient amount of said IGF-I to a mammalian host in need of such treatment.

4. The method of claim 3 wherein said mammalian host is a human host.

5. A method for improving the regeneration of transected peripheral nerves inn mammals by administering locally a therapeutically effective amount of insulin-like growth factor I (IGF-I) by infusion at a rate of 2.4 to 6 micrograms/day to a mammalian host in need of such treatment.

6. The method of claim 5 wherein said host is a human.

* * * * *